(12) United States Patent
Mueller et al.

(10) Patent No.: US 9,181,163 B2
(45) Date of Patent: Nov. 10, 2015

(54) HYDROGENATION OF KETONES HAVING AT LEAST A CARBON-CARBON DOUBLE BOND IN THE γ,δ-POSITION

(75) Inventors: Marc-André Mueller, Wehr (DE); Andreas Pfaltz, Basel (CH); Jonathan Medlock, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/125,954

(22) PCT Filed: Jun. 13, 2012

(86) PCT No.: PCT/EP2012/061226
§ 371 (c)(1),
(2), (4) Date: Mar. 28, 2014

(87) PCT Pub. No.: WO2012/171969
PCT Pub. Date: Dec. 20, 2012

(65) Prior Publication Data
US 2014/0249321 A1 Sep. 4, 2014

(30) Foreign Application Priority Data
Jun. 14, 2011 (EP) .................................. 11169784

(51) Int. Cl.
| | |
|---|---|
| *C07C 45/62* | (2006.01) |
| *C07C 29/143* | (2006.01) |
| *C07C 45/61* | (2006.01) |
| *C07C 49/04* | (2006.01) |
| *C07D 311/72* | (2006.01) |

(52) U.S. Cl.
CPC ............... *C07C 45/62* (2013.01); *C07C 29/143* (2013.01); *C07C 45/61* (2013.01); *C07C 49/04* (2013.01); *C07D 311/72* (2013.01)

(58) Field of Classification Search
CPC ...................................................... C07C 45/62
USPC .......................................................... 568/395
See application file for complete search history.

(56) References Cited

FOREIGN PATENT DOCUMENTS

WO    WO 2006/066863    6/2006

OTHER PUBLICATIONS

Mizaguchi et al., "An enzyme-catalyzed synthesis of natural [alpha]-tocopherol", *Tetrahedron: Asymmetry*, vol. 4, No. 9, Jan. 1, 1993, pp. 1961-1964.

Woodmansee et al., "Chiral pyridyl phosphinites with large aryl substituents as efficient ligands for the asymmetric iridium-catalyzed hydrogenation of difficult substrates", *Chemical Science*, vol. 1, May 12, 2010, pp. 72-78.
International Search Report for PCT/EP2012/061226, dated Jul. 26, 2012.

*Primary Examiner* — Taofiq A Solola
(74) *Attorney, Agent, or Firm* — Nixon & Vanderhye P.C.

(57) ABSTRACT

The present invention relates in a first aspect to a process for hydrogenation of ketones having at least a carbon-carbon double bond in the y,8-position to the keto group by hydrogen in the presence of at least one chiral iridium complex of formula (I), where R1 represents a group of formula (II) or (III) or (IV). It has been shown that this process leads to a strong increase in preferential formation of a single isomer. The process is particularly suitable for the hydrogenation of y,8-unsaturated ketones which can be used as flavors and fragrances or for the preparation of vitamin E and its derivatives or of flavors and fragrances.

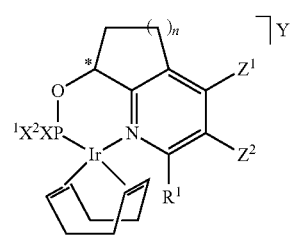

(I)

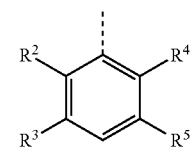

(II)

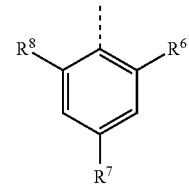

(III)

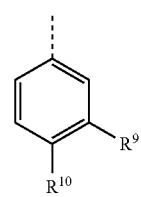

(IV)

12 Claims, No Drawings

HYDROGENATION OF KETONES HAVING AT LEAST A CARBON-CARBON DOUBLE BOND IN THE γ,δ-POSITION

This application is the U.S. national phase of International Application No. PCT/EP2012/061226 filed 13 Jun. 2012 which designated the U.S. and claims priority to EP Patent Application No. 11169784.3 filed 14 Jun. 2011, the entire contents of each of which are hereby incorporated by reference.

TECHNICAL FIELD

The present invention relates to the hydrogenation of γ,δ-unsaturated ketones, particularly suitable as flavours and fragrances or for the preparation of vitamin E and its derivatives.

BACKGROUND OF THE INVENTION

The hydrogenation of α,β-unsaturated ketones by hydrogen is known. The hydrogenation of ketones having at least a carbon-carbon double bond in the γ,δ-position to the keto group (=γ,δ-unsaturated ketones), however, differs strongly as the keto group and the double bond do not form a conjugated system. The carbon-carbon double bond is known in a majority of cases to be prochiral so that upon hydrogenation chiral centre(s) may be formed.

Hydrogenation products of such ketones having at least one carbon-carbon double bond play an important role particularly in the field of synthesis of vitamins, particularly of vitamins E and $K_1$. However, traditional known hydrogenations of such γ,δ-unsaturated ketones are unspecific and, hence, lead to formation of mixtures of isomers, the number of which dramatically increases as the number of chiral centres being formed by hydrogenation increases.

The (biological) activities of vitamins, however, are contributed mainly to only one or a few isomers out of the plurality of isomers. Hence, there exists a large interest to offer a method of hydrogenation allowing a selective formation of primarily one single isomer.

WO 2006066863 deals with the hydrogenation of alkenes using chiral iridium complexes. These chiral iridium complexes show a particularly good selectivity in the hydrogenation of olefins.

A large variety of chiral iridium complexes are disclosed in *Chem. Sci.*, 2010, 1, 72-78 where a large variety of trisubstituted olefins are hydrogenated in a asymmetrical manner. Apart from purely hydrocarbon substituted olefins, only certain ether, ester or hydroxyl functionalized olefins are disclosed to be hydrogenated by the use of said iridium complexes.

SUMMARY OF THE INVENTION

Therefore, the problem to be solved by the present invention is to offer a method for the hydrogenation of ketones having at least a carbon-carbon double bond in the γ,δ-position in an asymmetric way allowing the specific formation of a single isomer in a very high preference.

Surprisingly, it has been found that the process according to claim 1 is able to solve this problem.

It has been found that by using chiral iridium complexes having a specific aromatic substituent increases the selectivity of hydrogenation of the γ,δ-unsaturated ketones remarkably over known complexes.

In comparison to existing syntheses this increased selectivity combined with an extremely high conversion rate, particularly of 100%, allows a high yield in the desired isomer without, respectively with a strongly reduced amount of separation, is exceptional and is, hence, also very interesting from an economical and industrial point of view.

Further aspects of the invention form the subject of further independent claims. Preferred embodiments form the subject of dependent claims.

DETAILED DESCRIPTION OF THE INVENTION

The present invention relates in a first aspect to a process for hydrogenation of ketones having at least a carbon-carbon double bond in the γ,δ-position by hydrogen in the presence of at least one chiral iridium complex of formula (I)

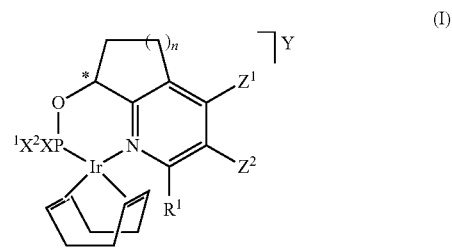

The index n is 1 or 2.

Furthermore $X^1$ and $X^2$ are independently from each other hydrogen atoms, $C_{1-5}$-alkyl, $C_{5-7}$-cycloalkyl, adamantyl, phenyl (optionally substituted with one to three $C_{1-4}$-alkyl, $C_{1-4}$-alkoxy, $C_{1-4}$-perfluoroalkyl groups and/or one to five halogen atoms)), benzyl, 1-naphthyl, 2-naphthyl, 2-furyl or ferrocenyl.

$Z^1$ and $Z^2$ are independently from each other hydrogen atoms, $C_{1-5}$-alkyl or $C_{1-5}$-alkoxy groups. It is preferred that $Z^1$ is $C_{1-5}$-alkyl or H and $Z^2$ is H. Most preferred $Z^1$ and $Z^2$ are both hydrogen atoms.

Y represents an anion, particularly selected from the group consisting of halide, $PF_6^-$, $SbF_6^-$, tetra(3,5-bis(trifluoromethyl)phenyl)borate $(BAr_F^-)$, $BF_4^-$, perfluorinated sulfonates, preferably $F_3C\text{—}SO_3^-$ or $F_9C_4\text{—}SO_3^-$; $ClO_4^-$, $Al(OC_6F_5)_4^-$, $Al(OC(CF_3)_3)_4^-$, $N(SO_2CF_3)_2^-$, $(SO_2C_4F_9)_2^-$ and $B(C_6F_5)_4^-$. Most preferably Y represents tetra(3,5-bis(trifluoromethyl)phenyl)borate, $Al(OC(CF_3)_3)_4^-$ or $B(C_6F_5)_4^-$.

$R^1$ represents a group of formula (II) or (III) or (IV)

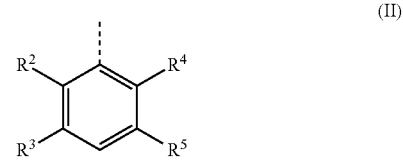

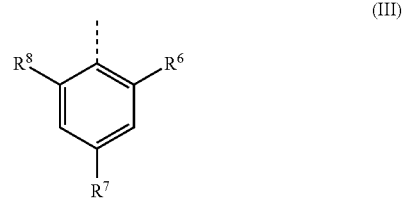

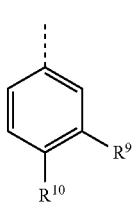
(IV)

wherein $R^2$ and $R^3$ represent either both H or an $C_1$-$C_4$-alkyl group or represent a divalent group forming together a 6-membered cycloaliphatic or an aromatic ring which optionally is substituted by halogen atoms or by $C_1$-$C_4$-alkyl groups or by $C_1$-$C_4$-alkoxy groups.

$R^4$ and $R^5$ represent a divalent group forming together a 6-membered cycloaliphatic or an aromatic ring which optionally is substituted by halogen atoms or by $C_1$-$C_4$-alkyl groups or by $C_1$-$C_4$-alkoxy groups.

$R^9$ and $R^{10}$ represent a divalent group forming together a 6-membered cycloaliphatic or an aromatic ring which optionally is substituted by halogen atoms or by $C_1$-$C_4$-alkyl groups or by $C_1$-$C_4$-alkoxy groups.

$R^6$ and $R^7$ and $R^8$ represent each a $C_1$-$C_4$-alkyl group.

Finally * represents the chiral centre of the catalyst of formula (I) and the dotted line represents the bond by which the substituent of formula (II), (III) or (IV) is bound to the rest of formula (I).

The term "independently from each other" in this document means, in the context of substituents, moieties, or groups, that identically designated substituents, moieties, or groups can occur simultaneously with a different meaning in the same molecule.

The anion tetra(3,5-bis(trifluoromethyl)phenyl)borate is abbreviated in the present document as "$BAr_F^-$" being known to the person skilled in the art also by the abbreviation "$[BAr^F_4]^-$".

The term "γ,δ-unsaturated ketones" is used in the present document as an equivalent for the term "ketones having at least a carbon-carbon double bond in the γ,δ-position to the keto group".

In the present document any dotted line represents the bond a substituent is bound to the rest of a molecule.

Ketones Having at Least a Carbon-Carbon Double Bond in the γ,δ-Position

The ketones having at least a carbon-carbon double bond in the γ,δ-position have two aliphatic carbon atoms between the keto group and the carbon-carbon double bond. Therefore, these ketones are particularly to be seen in contrast to the ketones having a carbon-carbon double bond in the α,β-position, also known to the person skilled in the art as α,β-unsaturated ketones having no aliphatic carbon atoms between the keto group and the carbon-carbon double bond.

Preferably the ketones having at least a carbon-carbon double bond in the γ,δ-position to the keto group have an additional alkyl substituent in the δ-position, i.e. the carbon atom in the δ-position does not have any hydrogen atoms attached directly to it.

The preferred ketones having at least a carbon-carbon double bond in the γ,δ-position are methyl ketones having at least a carbon-carbon double bond in the γ,δ-position.

Examples of such ketones having at least a carbon-carbon double bond in the γ,δ-position to the keto group are 5-hexen-2-one, 3,3-dimethyl-5-hexen-2-one, 5-methyl-5-hexen-2-one, 6-methyl-5-hepten-2-one, (E)-undec-5-en-2-one, 6,10-dimethyl-5,9-undecadien-2-one, 6,10,14,18-tetramethyl-5,9,13,17-nonadeca-tetraen-2-one, 6,10,14-trimethyl-5,9,13-pentadecatrien-2-one, 6,10-dimethyl-5,9-undecadien-2-one, or the ketones having formula (V) as listed below.

In a preferred embodiment the ketones having at least a carbon-carbon double bond in the γ,δ-position have the formula (V).

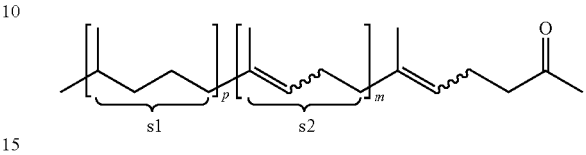
(V)

The indices m and p stand independently from each other for a value of 0 to 5, and a wavy line represents a carbon-carbon bond having either a Z or a E-configuration in respect to the double bond attached to said carbon-carbon bond and the substructures in formula (V) represented by s1 and s2 can be in any sequence.

By the term "the substructures in formula (V) represented by s1 and s2 can be in any sequence" is meant in the present document that also a compound of formula (V-1) or a formula (V-2) is covered by formula (V). Therefore, if several substructures s1 resp. s2, exist the individual substructures s1 resp. s2, can be arranged in an isolated manner, in blocks or randomly.

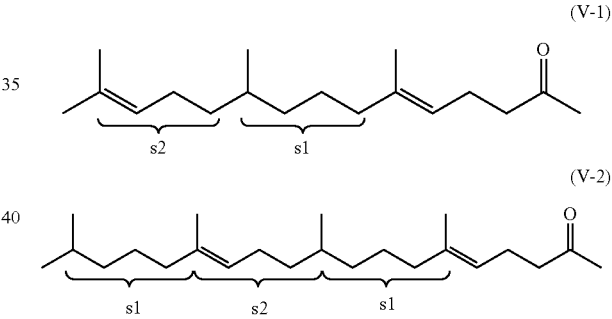
(V-1)

(V-2)

In case where the substructure substructures s1 comprises a chiral centre, it is preferred that said chiral centre is in a single specific configuration either R or S, particularly in the R-configuration.

Particularly the ketones having at least a carbon-carbon double bond in the γ,δ-position to the keto group are selected from the group consisting of 6-methylhept-5-en-2-one, (E)-6,10-dimethylundec-5-en-2-one, (Z)-6,10-dimethylundec-5-en-2-one, (E)-6,10-dimethylundeca-5,9-dien-2-one, (Z)-6,10-dimethylundeca-5,9-dien-2-one, (E)-6,10,14-trimethylpentadec-5-en-2-one, (Z)-6,10,14-trimethylpentadec-5-en-2-one; (5E,9E)-6,10,14-trimethylpentadeca-5,9-dien-2-one, (5E,9Z)-6,10,14-trimethylpentadeca-5,9-dien-2-one, (5Z,9E)-6,10,14-trimethylpentadeca-5,9-dien-2-one, (5Z,9Z)-6,10,14-trimethylpentadeca-5,9-dien-2-one; (E)-6,10,14-trimethylpentadeca-5,13-dien-2-one, (Z)-6,10,14-trimethylpentadeca-5,13-dien-2-one; (5E,9E)-6,10,14-trimethylpentadeca-5,9,13-trien-2-one, (5E,9Z)-6,10,14-trimethylpentadeca-5,9,13-trien-2-one, (5Z,9E)-6,10,14-trimethylpentadeca-5,9,13-trien-2-one, (5Z,9Z)-6,10,14-trimethylpentadeca-5,9,13-trien-2-one; (E)-6,10,14,18- tetramethylnonadec-5-en-2-one, (Z)-6,10,14,18-tetramethylnonadec-5-en-2-one; (5E,9E)-6,10,14,18-tetramethylnonadeca-5,9-dien-2-one, (5E,9Z)-6,10,14,18-tetramethylnonadeca-5,9-dien-2-one, (5Z,9E)-6,10,14,18-tetramethylnonadeca-5,9-dien-2-one, (5Z,9Z)-6,10,14,18-tetramethylnonadeca-5,9-dien-2-one; (5E,13E)-6,10,14,18-tetramethylnonadeca-5,13-dien-2-one, (5E,13Z)-6,10,14,18-tetramethylnonadeca-5,13-dien-2-one, (5Z,13E)-6,10,14,18-tetramethylnonadeca-5,13-dien-2-one, (5Z,13Z)-6,10,14,18-tetramethylnonadeca-5,13-dien-2-one; (E)-6,10,14,18-tetramethylnonadeca-5,17-dien-2-one, (Z)-6,10,14,18-tetramethylnonadeca-5,17-dien-2-one; (5E,9E,13E)-6,10,14,18-tetramethylnonadeca-5,9,13-trien-2-one, (5E,9E,13Z)-6,10,14,18-tetramethylnonadeca-5,9,13-trien-2-one, (5E,9Z,13E)-6,10,14,18-tetramethyl nonadeca-5,9,13-trien-2-one, (5E,9Z,13Z)-6,10,14,18-tetramethylnonadeca-5,9,13-trien-2-one, (5Z,9E,13E)-6,10,14,18-tetramethylnonadeca-5,9,13-trien-2-one, (5Z,9E,13Z)-6,10,14,18-tetramethylnonadeca-5,9,13-trien-2-one, (5Z,9Z,13E)-6,10,14,18-tetramethylnonadeca-5,9,13-trien-2-one, (5Z,9Z,13Z)-6,10,14,18-tetramethylnonadeca-5,9,13-trien-2-one; (5E,13E)-6,10,14,18-tetramethylnonadeca-5,13,17-trien-2-one, (5E,13Z)-6,10,14,18-tetramethylnonadeca-5,13,17-trien-2-one, (5Z,13E)-6,10,14,18-tetramethylnonadeca-5,13,17-trien-2-one, (5Z,13Z)-6,10,14,18-tetramethylnonadeca-5,13,17-trien-2-one; (5E,9E)-6,10,14,18-tetramethylnonadeca-5,9,17-trien-2-one, (5E,9Z)-6,10,14,18-tetramethylnonadeca-5,9,17-trien-2-one, (5Z,9E)-6,10,14,18-tetramethylnonadeca-5,9,17-trien-2-one, (5Z,9Z)-6,10,14,18-tetramethylnonadeca-5,9,17-trien-2-one; (5E,9E,13E)-6,10,14,18-tetramethylnonadeca-5,9,13,17-tetraen-2-one, (5E,9E,13Z)-6,10,14,18-tetramethylnonadeca-5,9,13,17-tetraen-2-one, (5E,9Z,13E)-6,10,14,18-tetramethylnonadeca-5,9,13,17-tetraen-2-one, (5E,9Z,13Z)-6,10,14,18-tetramethylnonadeca-5,9,13,17-tetraen-2-one, (ZE,9E,13E)-6,10,14,18-tetramethylnonadeca-5,9,13,17-tetraen-2-one, (5Z,9E,13Z)-6,10,14,18-tetramethylnonadeca-5,9,13,17-tetraen-2-one, (5Z,9Z,13E)-6,10,14,18-tetramethylnonadeca-5,9,13,17-tetraen-2-one, (5Z,9Z,13Z)-6,10,14,18-tetramethylnonadeca-5,9,13,17-tetraen-2-one, (5E,9E,13E)-6,10,14,18-tetramethylnonadeca-5,9,13-trien-2-one.

Preferably the ketone is (E)-6,10-dimethylundec-5,9-dien-2-one (geranylacetone) or (Z)-6,10-dimethylundec-5,9-dien-2-one (nerylacetone) or (5E,9E)-6,10,14-trimethylpentadeca-5,9,13-trien-2-one (E,E-farnesylacetone) or (5Z,9Z)-6,10,14-trimethylpentadeca-5,9,13-trien-2-one) (Z,Z-farnesylacetone) or (5E,9E)-6,10,14-trimethylpentadeca-5,9-dien-2-one or (5Z,9Z)-6,10,14-trimethylpentadeca-5,9-dien-2-one or (E)-6,10-dimethylundec-5-en-2-one or (Z)-6,10-dimethylundec-5-en-2-one or (E)-6,10,14-trimethylpentadec-5-en-2-one or (Z)-6,10,14-trimethylpentadec-5-en-2-one, preferably geranylacetone or E,E-farnesylacetone or (Z)-6,10-dimethylundec-5-en-2-one or (Z)-6,10,14-trimethylpentadec-5-en-2-one, more preferably geranylacetone or E,E-farnesylacetone.

Catalyst

The complex of formula (I) is neutral, i.e. the complex consist of a complex cation of formula (I') and anion Y as defined before.

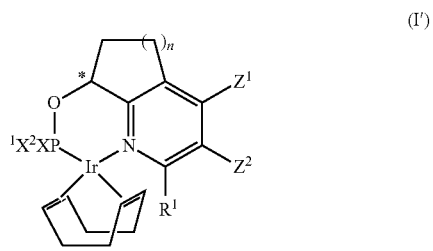

(I')

The person skilled in the art knows that anions and cations may be dissociated. For a better and easier reading's sake any charges of formulae have hence been omitted elsewhere in the present document.

$X^1$ and/or $X^2$ represent preferably hydrogen atoms, methyl, ethyl, iso-propyl, n-butyl, iso-butyl, tert-butyl, n-pentyl, iso-pentyl, neopentyl, cyclohexyl, adamantly, phenyl, benzyl, o-tolyl, m-tolyl, p-tolyl, 4-methoxyphenyl, 4-trifluoromethylphenyl, 3,5-di-tert-butylphenyl, 3,5-dimethoxyphenyl, 1-naphthyl, naphthyl, 2-furyl, ferrocenyl or a phenyl group which is substituted with one to five halogen atoms.

In case of $X^1$ and/or $X^2$ represents a phenyl group which is substituted with one to five halogen atoms particularly useful are the phenyl groups substituted by fluorine atoms, i.e. $C_6H_4F$, $C_5H_3F_2$, $C_5H_2F_3$, $C_5HF_4$ or $C_5F_5$.

In case of $X^1$ and/or $X^2$ represents a phenyl group which is substituted with one to three $C_{1-4}$-alkyl, particularly useful are the phenyl groups substituted by methyl group(s), particularly ortho-tolyl and para-tolyl.

Preferably $X^1$ and $X^2$ represent both the same substituent.

Most preferred $X^1$ and $X^2$ are both phenyl or both ortho-tolyl groups.

It has been found that one of the key features of the catalyst of formula (I) is the specific substituent $R^1$.

It is preferred that the $C_1$-$C_4$-alkyl or alkoxy groups used in the definition of $R^2$, $R^3$, $R^4$, $R^5$, $R^6$, $R^7$, $R^8$, $R^9$ and $R^{10}$ above are primary or secondary, preferably primary, alkyl or alkoxy groups.

A particularly suited substituent $R^1$ of formula (II) is the 9-anthryl or 1-naphthyl group.

A further particularly suited substituent $R^1$ of formula (III) is the mesityl group.

A further particularly suited substituent $R^1$ of formula (IV) is the 1-naphthyl group.

Preferably $R^1$ is represented by formula (II a) or (II b) or (III a), particularly (II a) or (III a).

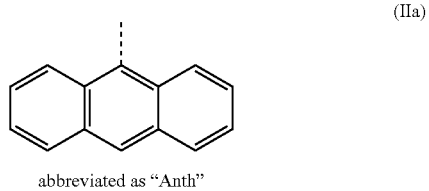

(IIa)

abbreviated as "Anth"

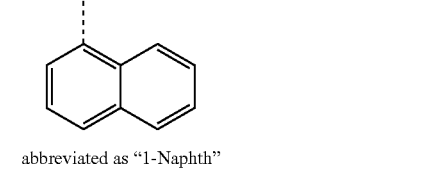

(IIb)

abbreviated as "1-Naphth"

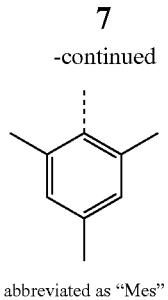

abbreviated as "Mes"

It has been found that the most preferred substituent $R^1$ is 9-anthryl, i.e. $R^1$ is most preferably represented by formula (IIa).

The preferred chiral iridium complex of formula (I) are the complexes of formulae (I-A), (I-B), (I-C) and (I-D).

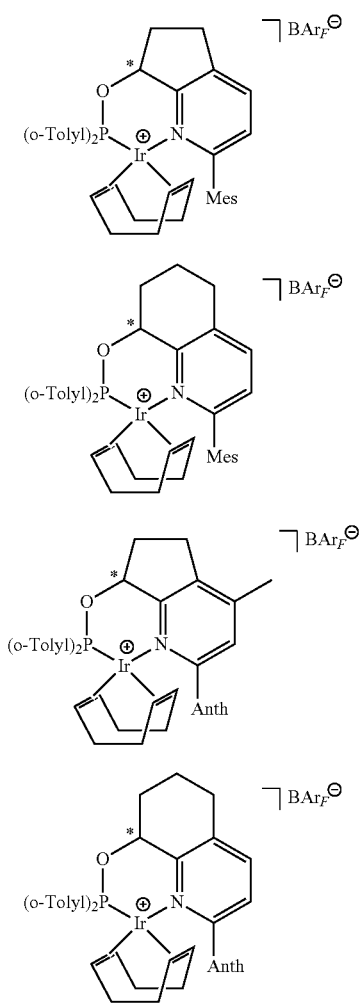

Most preferred as chiral iridium complexes of formula (I) are the complexes of formulae (I-C) and (I-D), particularly the one of formula (I-C).

The chiral iridium complexes of formula (I) can be synthesized accordingly as described in detail in *Chem. Sci.*, 2010, 1, 72-78 whose entire content is hereby included by reference.

The iridium complex of formula (I) is chiral. The chirality at said chiral centre marked by the asterisk is either S or R, i.e. there exist two isomers (Ia) and (Ib) of the chiral complex of formula (I):

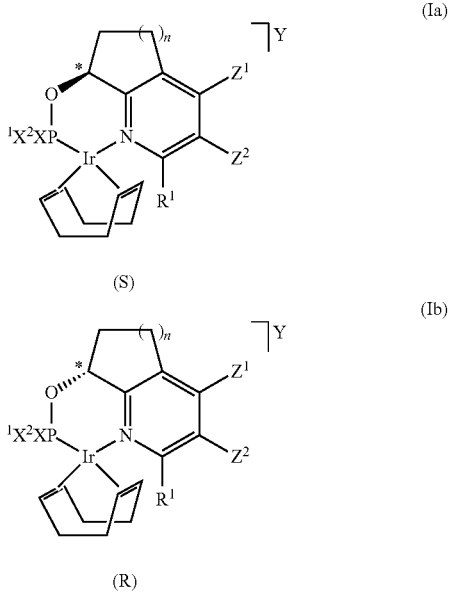

The individual isomers of the complex of formula (I) could be principally separated after the complexation step from a isomeric mixture. However, as *Chem. Sci.*, 2010, 1, 72-78 discloses, the synthesis of the complex of formula (I) involves a reaction involving a chiral alcohol. As it is known that the further reaction steps do not modify the chirality of the complex its isomeric purity (S:R-ratio) is governed therefore by the enantiomeric purity of said alcohol. As said corresponding alcohol can be obtained in a R/S ratio of more than 99% resp. lower than 1%, the complex of formula (I) can be obtained in extremely high enantiomeric purities, particularly in a R/S ratio of more than 99% resp. lower than 1%.

The chiral iridium complex is preferably used in an excess of one enantiomer.

Particularly, it is preferred that the ratio of the molar amounts of the individual enantiomers R:S of the catalyst (I) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

In one embodiment the chiral centre indicated by * has the R-configuration.

In another embodiment the chiral centre indicated by * has the 5-configuration.

Hydrogenation

The hydrogenating agent is hydrogen ($H_2$).

The amount of catalyst is preferably from about 0.001 to about 5 mol %, preferably from about 0.01 to about 2 mol %, more preferably from about 0.1 to about 1 mol-%, based on the amount of the ketone.

The hydrogenation can be carried out in substance or in an inert carrier, particularly in an inert solvent.

Preferred suitable solvents are halogenated hydrocarbons, hydrocarbons, carbonates, ethers and halogenated alcohols.

Particularly preferred solvents are hydrocarbons, fluorinated alcohols and halogenated hydrocarbons, particularly halogenated aliphatic hydrocarbons.

Preferred examples of hydrocarbons are hexane, heptane, toluene, xylene and benzene, particularly toluene.

Preferred ethers are dialkylethers. Particularly useful ethers are dialklyethers with less than 8 carbon atoms. Most preferred ether is methyl tert.-butyl ether ($CH_3$—O—C($CH_3$)$_3$).

Preferred halogenated alcohols are fluorinated alcohols. A particularly preferred fluorinated alcohol is 2,2,2-trifluoroethanol.

One preferred group of halogenated hydrocarbon are halogenated aromatic compounds, particularly chlorobenzene.

Preferred examples of halogenated aliphatic hydrocarbons are mono- or polyhalogenated linear or branched or cyclic $C_1$- to $C_{15}$-alkanes. Especially preferred examples are mono- or polychlorinated or -brominated linear or branched or cyclic $C_1$- to $C_{115}$-alkanes. More preferred are mono- or polychlorinated linear or branched or cyclic $C_1$- to $C_{15}$-alkanes. Most preferred are dichloromethane, 1,2-dichloroethane, 1,1,1-trichloroethane, chloroform, and methylene bromide.

The most preferred solvent for the hydrogenation is dichloromethane.

The amount of solvent used is not very critical. However, it has been shown that the concentration of the ketone having at least a carbon-carbon double bond in the γ,δ-position to the keto group is preferably between 0.05 and 1 M, particularly between 0.2 and 0.7 M.

The hydrogenation reaction is conveniently carried out at an absolute pressure of hydrogen from about 1 to about 100 bar, preferably at an absolute pressure of hydrogen from about 20 to about 75 bar. The reaction temperature is conveniently between about 0 to about 100° C., preferably between about 10 to about 40° C.

The sequence of addition of the reactants and solvent is not critical.

The technique and apparatus suitable for the hydrogenation is principally known to the person skilled in the art.

Hydrogenated Ketone

A further aspect of the present invention is a hydrogenated ketone which is obtained by the hydrogenation process as described above. Within this hydrogenation process the carbon-carbon double bond in the γ,δ-position to the keto group is hydrogenated.

If the ketone having at least a carbon-carbon double bond in the γ,δ-position to the keto group has an alkyl substituent in the δ-position to the keto group, particularly being a ketone of formula (V), a chiral centre is produced in the δ-position of the hydrogenated product.

It has been found that by choosing a specific chirality (R or S; chiral centre indicated by *) of the catalyst of formula (I) a specific chirality of the hydrogenated ketone, particularly of formula (V), can be achieved.

It has been also found that ratio of isomers at that chiral centre of the ketone being formed strongly depends on the ratio of isomers (centre indicated by *) of the catalyst of formula (I).

Aiming to achieve very high stereospecific preferential formation of specific isomers in the hydrogenated ketone it is, therefore, preferred that the ratio of the molar amounts of the individual enantiomers R:S of the catalyst (I) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

Therefore, it is preferred that the hydrogenated ketone a ratio of R:S isomers at the chiral centre in the δ-position of more than 80:20 or less than 20:80, preferably in the range 100:0 to 90:10 or in the range of 0:100 to 10:90. Most preferred is that this ratio is in the range of 100:0 to 98:2 or in the range of 2:98 to 0:100. Particularly the ratio is about 100:0 or about 0:100. The ultimately preferred ratio is 100:0 or 0:100.

It has, surprisingly, been found that for the hydrogenation of an γ,δ-unsaturated ketone with (E) configuration, the R-isomer of the complex of formula (I) leads to the formation of the isomer having S-configuration at the carbon situated in the δ-position of the hydrogenated ketone, particularly of formula (V), and that for the hydrogenation of an γ,δ-unsaturated ketone with (E) configuration, the S-isomer of the complex of formula (I) leads to the formation of the isomer having R-configuration at the carbon situated in the δ-position of the hydrogenated ketone, particularly of formula (V).

Furthermore, it has been found that for the hydrogenation of an γ,δ-unsaturated ketone with (Z) configuration, the R-isomer of the complex of formula (I) leads to the formation of the isomer having R-configuration at the carbon situated in the δ-position of the hydrogenated ketone, particularly of formula (V), and that for the hydrogenation of an γ,δ-unsaturated ketone with (Z) configuration, the S-isomer of the complex of formula (I) leads to the formation of the isomer having S-configuration at the carbon situated in the δ-position of the hydrogenated ketone, particularly of formula (V).

Specifically, it has been found that using the R-isomer of catalyst of formula (I) in the hydrogenation of E-geranyl acetone (=(E)-6,10-dimethylundeca-5,9-dien-2-one) the hydrogenation product (6S)-6,10-dimethylundecan-2-one is formed in more than 98% in respect to all of the possible stereoisomers (i.e. (6S)-6,10-dimethylundecan-2-one and (6R)-6,10-dimethylundecan-2-one) whereas the corresponding R-isomer is obtained only in amount of less than 2%.

If the corresponding S-isomer of catalyst of formula (I) is used in the hydrogenation of geranylacetone the hydrogenation leads to the correspondingly high yield in the R-isomer of the hydrogenated product.

In case where the ketones having at least a carbon-carbon double bond in the γ,δ-position to the keto group have further carbon-carbon double bond(s), such as those of formula (V) in which m is different from 0, depending on the process parameters said additional carbon-carbon double bond(s) are hydrogenated or not.

It is preferred, though, that the hydrogenated ketone has no carbon-carbon double bond remaining.

In case where additional carbon-carbon double bond(s) are present in the ketone having at least a carbon-carbon double bond in the γ,δ-position to the keto group further chiral centres may be formed. This is particularly the case where in said additional double bonds contain carbon atoms without hydrogen atoms being attached to them are present.

This is particularly the case in ketones of formula (V) in which the index m is different from 0. Therefore, the number of chiral centres being formed by the described hydrogenation is maximal m+1.

Surprisingly, it has been found that the specific chirality being formed by the hydrogenation of those additional carbon-carbon double bonds is also governed by the chirality of the complex of formula (I).

In analysing the isomers being formed it has been found that particularly one isomer is preferably formed.

Hence, aiming to enhance the yield of a single isomer in the hydrogenated ketone it is preferred to increase the ratio, R/S resp. S/R (at centre indicated by *) in the chiral complex of formula (I).

Hence, it is preferred that in the hydrogenated ketone one isomer is formed in an amount of more than 80%, more preferably more than 90% in respect to all of the possible stereoisomers.

Specifically, it has been found that using the R-isomer of catalyst of formula (I) in the hydrogenation of E,E-farnesylacetone (=(5E,9E)-6,10,14-trimethylpentadeca-5,9,13-trien-2-one) the hydrogenation product (6S,10S)-6,10,14-trimethylpentadecan-2-one is formed in more than 96% in respect to all of the possible stereoisomers (i.e. (6S,10S)-6,10,14-trimethylpentadecan-2-one, (6S,10R)-6,10,14-trimethylpentadecan-2-one, (6R,10S)-6,10,14-trimethylpentadecan-2-one and (6R,10R)-6,10,14-trimethylpentadecan-2-one). Hence, the corresponding (6S,10R)- and (6R,10S)- and (6R,10R)-isomers are only formed only in smaller amounts.

If the corresponding S-isomer of catalyst of formula (I) is used in the hydrogenation of E,E-farnesylacetone the hydrogenation leads to more than 96% of the corresponding (6R,10R)-isomer, in respect to all of the possible stereoisomers.

It is important to realize that the present invention enables a further increase of selectivity in view of the state of the art. This increase, however, has a large technical impact and is technically much more challenging than an increase on lower level (for example an increase from 98% to 99% is much more challenging to achieve than an increase from 50% to 51%). Particularly, if there are more than 1 chiral centres involved, the impact on increase of 1% is technically even more pronounced.

The preferred hydrogenated ketones are 6,10-dimethylundecan-2-one or 6,10,14-trimethylpentadecan-2-one.

As particularly a (6R)-6,10-dimethylundecan-2-one, respectively (6R,10R)-6,10,14-trimethylpentadecan-2-one, are most preferred isomers to be formed by the described hydrogenation process from geranyl acetone, respectively from E,E-farnesyl acetone, the catalyst of formula (I), particularly of formula (I-C) or (I-D), has in a preferred embodiment the S-configuration at the chiral centre indicated by *.

The hydrogenated ketones are suitable for different use.

One further aspect of the invention relates to the use of the hydrogenated ketones described in detail above as flavours and fragrances or for the preparation of flavours and fragrances.

One further and preferred aspect of the invention relates to the use of the hydrogenated ketones described before in detail for the preparation of preparation of vitamin E and its derivatives.

Particularly the hydrogenated ketones derived from geranylacetone and farnesylacetone represent important intermediates in the multi step synthesis of vitamin E and its derivatives.

According to one method of multi step synthesis of vitamin E, hexahydrofarnesylacetone (=6,10,14-trimethylpentadecan-2-one) is converted to isophytol which than can be used directly or according to an alternative synthesis its isomerized product, i.e. phytol, to yield in a further reaction step vitamin E as disclosed for example in Ullmann's Encyclopedia of Industrial Chemistry, Release 2010, 7$^{th}$ Edition, "Vitamins", page 44-46.

Therefore, the method of preparing isophytol from 6,10,14-trimethylpentadecan-2-one, which is prepared by a process for hydrogenation of farnesyl acetone as described above, represent a further aspect of the present invention. Isophytol is an important intermediate in the synthesis of vitamin E and K.

Therefore, the present invention relates also to a process of preparing isophytol comprising a step of hydrogenation of ketones having at least a carbon-carbon double bond in the γ,δ-position to the keto group, particularly from farnesyl acetone or geranyl acetone, by hydrogen in the presence of at least one chiral iridium complex of formula (I) as described before in detail. Particularly this process comprises the step of hydrogenation of ketones having at least a carbon-carbon double bond in the γ,δ-position to the keto group by hydrogen in the presence of at least one chiral iridium complex of formula (I) yielding 6,10-dimethylundecan-2-one or 6,10,14-trimethylpentadecan-2-one.

A further important use of the hydrogenated ketones derived from geranyl acetone and farnesyl acetone represent important intermediates in the multi step synthesis of vitamin E and its derivatives.

Hence, a method of preparing vitamin E or its derivatives in a multi step synthesis which comprises a reaction step with a hydrogenated ketone as described above represents a further aspect of the present invention.

As isophytol is not only an important intermediate in the synthesis of vitamin E but also of vitamin $K_1$, a method of preparing vitamin $K_1$ or its derivatives in a multi step synthesis which comprises a reaction step with a hydrogenated ketone as described above represents also a further aspect of the present invention.

Therefore, the present invention relates also to a process of preparing vitamin E or its derivatives or vitamin $K_1$ or its derivatives comprising the step of hydrogenation of ketones having at least a carbon-carbon double bond in the γ,δ-position to the keto group by hydrogen in the presence of at least one chiral iridium complex of formula (I) as described before in detail. Particularly this process comprises the step of hydrogenation of ketones having at least a carbon-carbon double bond in the γ,δ-position to the keto group, particularly from farnesyl acetone or geranyl acetone, by hydrogen in the presence of at least one chiral iridium complex of formula (I) yielding 6,10-dimethylundecan-2-one or 6,10,14-trimethylpentadecan-2-one.

Hence, the present invention relates also to a process of preparing vitamin E or its derivatives or vitamin $K_1$ or its derivatives in a multi step synthesis which comprises a reaction step of hydrogenation of ketones having at least a carbon-carbon double bond in the γ,δ-position to the keto group by hydrogen in the presence of at least one chiral iridium complex of formula (I) as described before in detail.

As described before in detail, the present invention allows synthesizing stereospecifically a specific chiral isomer of a hydrogenated ketone in a very efficient way.

Naturally occurring vitamin E has in all the chiral centres indicated by ✸ in formula (VI) the R-configuration.

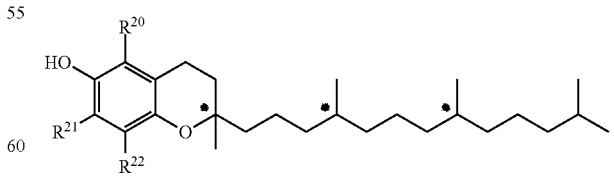

(VI)

α-Tocopherol ($R^{20}$=$R^{21}$=$R^{22}$=$CH_3$), β-Tocopherol ($R^{20}$=$R^{22}$=$CH_3$, $R^{21}$=H), γ-Tocopherol ($R^{20}$=H, $R^{21}$=$R^{22}$=$CH_3$), δ-Tocopherol ($R^{20}$=$R^{21}$=H, $R^{22}$=$CH_3$)

Vitamin K₁ has two chiral centres marked by # in formula (VII).

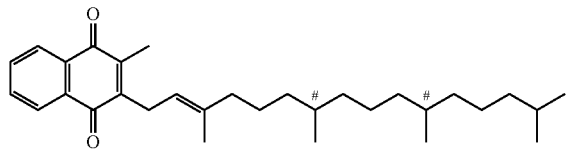

(VII)

Vitamins E and K₁ produced by other known processes provide a mixture of a large number of stereoisomers (8 resp. 4) originating from different configuration at the centres indicated by ✱, resp. by #, in formula (VI) resp. (VII).

By offering a synthetic route according to the present invention using hydrogenated ketones being prepared in a stereospecific manner, it is now possible to offer a synthetic method to supply vitamin K₁ directly in a specific configuration, particularly in the all R-configuration, at all chiral centres indicated by # in formula (VII) in a much higher yield, and hence no, respectively much less, further separation is needed to supply one single isomer having the desired configuration (i.e. all R).

Furthermore, it is possible now to offer also a synthetic way of vitamin E and its derivatives from cheap basic chemicals, in a unique stereospecific manner, in a mixture of essentially only two isomers. These two isomers differ only in the configuration in the 2 position in formula (VI), i.e. in the chiral centre ✱ adjacent directly to the ether oxygen atom, and are due to the final reaction step in the synthesis of vitamin E. The fact, however, that only 2 isomers are delivered instead of 8 isomers, leads on the one hand to a much higher overall yield of desired all R-isomer (50% instead of about 12.5%) and on the other hand to the advantage that only two isomers need to be separated which is technically much easier and more efficient and particularly in a much more cost effect way than isomeric mixtures resulted by traditional processes. Therefore, the present invention is highly interesting from a economical point of view.

Particularly preferred is (all-R)-α-Tocopherol (=(2R,4'R,8'R)-α-Tocopherol or briefly (R,R,R)-α-Tocopherol).

Examples

The invention is further illustrated by the following examples.

Starting Products

The catalysts of formula (I-A), (I-B), (I-C) and (I-D) and the catalysts of comparison of formula (Ref-A) and (Ref-B) used in the examples have been prepared according to the procedure described in *Chem. Sci.*, 2010, 1, 72-78.

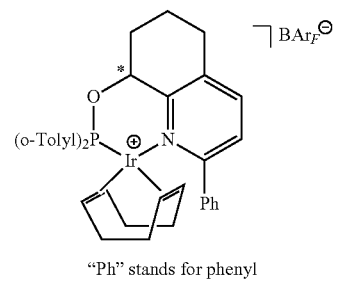

(Ref-A)

"Ph" stands for phenyl

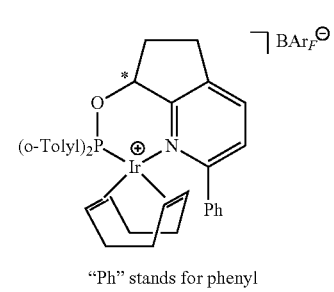

(Ref-B)

"Ph" stands for phenyl

The complexes used have an R/S ratio of more than 99%, resp. less than 1% (based on the R/S-ratio of the chiral alcohol used in its synthesis).

Geranylacetone (99.2% (GC)) and E,E-farnesyl acetone (>98% (GC)) were prepared by DSM Nutritional Products, Lalden/Sisseln, Switzerland.

Analysis of the Hydrogenated Reaction Products

The conversion of the hydrogenation reaction was determined by gas chromatography using an achiral column. For the determination of the isomer ratio, the hydrogenated ketones were reacted with either (+)-diisopropyl O,O'-bis(trimethylsilyl)-L-tartrate or (−)-diisopropyl O,O'-bis(trimethylsilyl)-D-tartrate in the presence of trimethylsilyl triflate [Si(CH₃)₃(OSO₂CF₃)] to form the diastereomeric ketals as described in A. Knierzinger, W. Walther, B. Weber, R. K. Müller, T. Netscher, Helvetica Chimica Acta 1990, 73, 1087-1107. The ketals were analysed by gas chromatography using an achiral column to determine the isomer ratios.

For the hydrogenated ketone 6,10-dimethylundecan-2-one, either D-(−) or L-(+) diisopropyltartrate can be used.

For 6,10,14-trimethylpentadecan-2-one, L-(+) diisopropyltartrate was used to measure the quantity of the (6R,10R) isomer that was present. This method, however, was not able to separate all four isomers of 6,10,14-trimethylpentadecan-2-one. Hence, the amount of the (6S,10S)-isomer and of the (6R,10S)-isomer could only be measured as a sum and are reported in the tables 1, 4, 5, 6 and 7 as "((SS)+(RS))".

D-(−) diisopropyltartrate was used to determine the amount of the (6S,10S) isomer. This method, however, was not able to separate all four isomers of 6,10,14-trimethylpentadecan-2-one. Hence, the amount of the (6R,10R)-isomer and of the (6S,10R)-isomer could only be measured as a sum and are reported in the tables 1, 4, 5 and 6 as "((RR)+(SR))".

Thus the selectivity of the stereoselective hydrogenation was determined indirectly.

Chromatography

Method for Conversion:

Agilent 7890A GC equipped with FID. Agilent HP-5 column (30 m, 0.32 mm diameter, 0.25 μm film thickness) with 25 psi hydrogen carrier gas. The samples were injected as solutions in dichloromethane with a split ratio of 10:1. Injector temperature: 250° C., detector temperature: 300° C. Oven temperature program: 50° C. (2 min) then 15° C./min to 300° C., hold 5 min.

Method for Determination of Isomers:

Agilent 6890N GC with FID. Agilent CP-Sil88 for FAME column (60 m, 0.25 mm diameter, 0.20 μm film thickness) with 16 psi hydrogen carrier gas. The samples were injected as solutions in ethyl acetate with a split ratio of 5:1. Injector temperature: 250° C., FID detector temperature: 250° C. Oven temperature program: 165° C. (isothermal, 240 min)

Hydrogenation

In an autoclave 0.25 mmol of (E)-geranylacetone, respectively E,E-farnesyl acetone, and 0.5, resp. 1 mol-% of the Ir complex and 1.25 ml of absolute (dry) dichloromethane were put. The autoclave was closed and a pressure of 50 bar of hydrogen was applied. Under stirring the reaction solution was kept at room temperature for 14 hours. Afterwards the pressure was released and the solvent removed. For determining the conversion the crude product was analysed by achiral gas chromatography without any further purification. If the reaction was complete, the product was converted into the ketal as described above in detail.

TABLE 1

Hydrogenation of E,E-farnesyl acetone.

|  | Ref. 1 | Ref. 2 | 1 | Ref. 3 | 2 | 3 | 4 |
|---|---|---|---|---|---|---|---|
| Formula of Ir-catalyst | Ref-A | Ref-A | I-D | Ref-B | I-A | I-C | I-C |
| Configuration at* | R | R | R | S | S | S | S |
| Amount catalyst [mol-%] | 0.5 | 1.0 | 0.5 | 1.0 | 0.5 | 0.5 | 1.0 |
| Conversion [%] | 100 | 100 | 100 | 100 | 100 | 100 | 100 |
| Isomer-Distribution[1] |  |  |  |  |  |  |  |
| (SS) [%] | 96.7 | 96.6 | 97.4 |  |  |  |  |
| ((RR) + (SR)) [%] | 0.8 | 1.2 | 0.5 |  |  |  |  |
| (RS) [%] | 2.5 | 2.2 | 2.1 |  |  |  |  |
| (RR) [%] |  |  |  | 84.0 | 96.1 | 98.3 | 98.5 |
| ((SS) + (RS)) [%] |  |  |  | 14.2 | 2.9 | 0.3 | 0.2 |
| (SR) [%] |  |  |  | 1.8 | 1.0 | 1.4 | 1.3 |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

TABLE 2

Hydrogenation of E-geranylacetone.

|  | Ref. 4 | 5 | 6 |
|---|---|---|---|
| Formula of Ir-catalyst | Ref-A | I-C | I-D |
| Configuration at * | S | S | R |
| Amount catalyst [mol-%] | 0.5 | 0.5 | 0.5 |
| Conversion [%] | 100 | 100 | 100 |
| Isomer-Distribution |  |  |  |
| (6R)-6,10-dimethylundecan-2-one [%] | 96.5 | >98 | <2 |
| (6S)-6,10-dimethylundecan-2-one [%] | 3.5 | <2 | >98 |

The results of table 1 show clearly that the process according to the invention yields in a quantitative conversion a mixture of isomers which consist almost completely of one single specific isomer. It is also visible that selection of the substituent $R^1$ in formula (I) is of key importance and shows that particularly the 9-anthryl group yields to a dramatically higher selectivity than the phenyl group.

Examples 2-4 have been used to synthesize (R,R)-isophytol and further in a high yield to a binary mixture of 2R,4'R,8'R-α-tocopherol and 2S,4'R,8'R-α-tocopherol.

Further Examples of Hydrogenation

In an autoclave 0.25 mmol of (E)-6,10-dimethylundec-5-en-2-one (E-dihydrogeranylacetone), respectively (5E,9E)-6,10,14-trimethylpentadeca-5,9,13-trien-2-one (E,E-farnesylacetone) (EE-FA), respectively (5Z,9Z)-6,10,14-trimethylpentadeca-5,9,13-trien-2-one (Z,Z-farnesylacetone) (ZZ-FA), respectively (5E,9E)-6,10,14-trimethylpentadeca-5,9-dien-2-one (E,E-dihydrofarnesylacetone) (EE-DHFA) respectively (5Z,9Z)-6,10,14-trimethylpentadeca-5,9-dien-2-one (Z,Z-dihydrofarnesylacetone) (ZZ-DHFA), respectively (10R,E)-6,10,14-trimethylpentadec-5-en-2-one, and 1 mol-% of the Ir complex and 1.25 ml of absolute (dry) dichloromethane (DCM), respectively 2,2,2-trifluoroethanol (TFE) were put. The autoclave was closed and a pressure of 50 bar of hydrogen was applied. Under stirring the reaction solution was kept at room temperature for 12-18 hours. Afterwards the pressure was released and the solvent removed. For determining the conversion the crude product was analysed by achiral gas chromatography without any further purification. If the reaction was complete, the product was converted into the ketal as described above in detail.

Dihydrogeranylacetone and dihydrofarnesylacetone are prepared according to example 1, respectively 2, of U.S. Pat. No. 6,329,554. The individual isomers of dihydrogeranylacetone, dihydrofarnesylacetone and farnesylacetone are then separated by chromatographic techniques respectively by distillation. The chemical purity of all samples is greater than 99%. The isomeric purity of the alkene is minimum 99%.

(10R,E)-6,10,14-trimethylpentadec-5-en-2-one (R-THFA) has been prepared from (3RS,7R)-3,7,11-trimethyl-1-dodecen-3-ol (=(7R)-tetrahydronerolidol) according to the method disclosed in example 2 of U.S. Pat. No. 6,329,554, which in return has been prepared from (6R)-6,10-dimethylundecan-2-one of example 5 according the method disclosed for compound (VII) in Ofner (A. Ofner et al, Helv. Chim. Acta. 1959, 2577-2584). (10R,E)-6,10,14-trimethylpentadec-5-en-2-one obtained by this method showed a R:S ratio of 98:2 at the C10 centre.

TABLE 3

Hydrogenation of (E)-6,10-dimethylundec-5-en-2-one.

|  | Ref. 5 | 7 | Ref. 6 | 8 | 9 |
|---|---|---|---|---|---|
| Formula of Ir-catalyst | Ref-A | I-D | Ref-A | I-D | I-C |
| Configuration at * | R | R | R | S | S |
| Amount catalyst [mol-%] | 1 | 1 | 1 | 1 | 1 |
| Solvent | TFE | TFE | DCM | DCM | DCM |
| Conversion [%] | 100 | 100 | 100 | 100 | 100 |
| Isomer-Distribution |  |  |  |  |  |
| (6R)-6,10-dimethylundecan-2-one [%] | 1.4 | 0.7 | 2.3 | 98.6 | 98.9 |
| (6S)-6,10-dimethylundecan-2-one [%] | 98.6 | 99.3 | 97.7 | 1.4 | 1.1 |

TABLE 4

Hydrogenation of
(5E,9E)-6,10,14-trimethylpentadeca-5,9,13-trien-2-one (EE-FA),
(5Z,ZE)-6,10,14-trimethylpentadeca-5,9,13-trien-2-one (ZZ-FA).

|  | Ref. 7 | 10 | Ref. 8 | 11 |
|---|---|---|---|---|
| Formula of Ir-catalyst | Ref-A | I-D | Ref-A | I-D |
| Substrate | EE-FA | EE-FA | ZZ-FA | ZZ-FA |
| Configuration at * | R | R | R | R |
| Amount catalyst [mol-%] | 1 | 1 | 1 | 1 |
| Solvent | TFE | TFE | TFE | TFE |
| Conversion [%] | 100 | 100 | 100 | 100 |
| Isomer-Distribution[1] | | | | |
| (SS) [%] | 96.9 | 99.1 | | |
| ((RR) + (SR)) [%] | 1.4 | 0.1 | | |
| (RS) [%] | 1.7 | 0.8 | | |
| (RR) [%] | | | 94.4 | 95.1 |
| ((SS) + (RS)) [%] | | | 2.2 | 1.8 |
| (SR) [%] | | | 3.4 | 3.1 |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

TABLE 5

Hydrogenation of
(5E,9E)-6,10,14-trimethylpentadeca-5,9-dien-2-one (EE-DHFA).

|  | Ref. 9 | 12 | 13 | Ref. 10 | 14 |
|---|---|---|---|---|---|
| Formula of Ir-catalyst | Ref-A | I-D | I-C | Ref-A | I-D |
| Substrate | EE-DHFA | EE-DHFA | EE-DHFA | EE-DHFA | EE-DHFA |
| Configuration at * | R | R | S | R | R |
| Amount catalyst [mol-%] | 1 | 1 | 1 | 1 | 1 |
| Solvent | DCM | DCM | DCM | TFE | TFE |
| Conversion [%] | 100 | 100 | 100 | 100 | 100 |
| Isomer-Distribution[1] | | | | | |
| (SS) [%] | 92.1 | 94.6 | | 93.4 | 95.6 |
| ((RR) + (SR)) [%] | 5.5 | 4.4 | | 5.5 | 4.4 |
| (RS) [%] | 2.3 | 1.01 | | 1.1 | 0.0 |
| (RR) [%] | | | 94.5 | | |
| ((SS) + (RS)) [%] | | | 4.7 | | |
| (SR) [%] | | | 0.9 | | |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

The results of tables 3, 4, 5 and 6 show that the hydrogenation of the present invention leads to higher selectivity. Furthermore, these results show also the beneficial effect of 2,2,2-trifluoroethanol as compared to dichloromethane for the increase of selectivity.

They also show that the hydrogenation of an γ,δ-unsaturated ketone with (E) configuration, the R-isomer of the Ir-complex leads to the formation of the isomer having S-configuration at the carbon situated in the 6-position of the hydrogenated ketone, respectively, the S-isomer of the Ir-complex leads to the formation of the isomer having R-configuration at the carbon situated in the δ-position of the hydrogenated ketone.

TABLE 6

Hydrogenation of
(5Z,9Z)-6,10,14-trimethylpentadeca-5,9-dien-2-one (ZZ-DHFA).

|  | Ref. 11 | 15 | 16 | Ref. 12 | 17 | 18 |
|---|---|---|---|---|---|---|
| Formula of Ir-catalyst | Ref-A | I-D | I-C | Ref-A | I-D | I-C |
| Substrate | ZZ-DHFA | ZZ-DHFA | ZZ-DHFA | ZZ-DHFA | ZZ-DHFA | ZZ-DHFA |
| Configuration at * | R | R | S | R | R | S |
| Amount catalyst [mol-%] | 1 | 1 | 1 | 1 | 1 | 1 |
| Solvent | DCM | DCM | DCM | TFE | TFE | TFE |
| Conversion [%] | 100 | 100 | 100 | 100 | 100 | 100 |
| Isomer-Distribution[1] | | | | | | |
| (SS) [%] | | | 96.5 | | | 97.1 |
| ((RR) + (SR)) [%] | | | 1.3 | | | 1.3 |
| (RS) [%] | | | 2.2 | | | 1.7 |
| (RR) [%] | 96.0 | 96.6 | | 96.3 | 97.2 | |
| ((SS) + (RS)) [%] | 1.8 | 1.2 | | 1.7 | 1.3 | |
| (SR) [%] | 2.2 | 2.2 | | 2.0 | 1.6 | |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

Similarly, they show also that the hydrogenation of an γ,δ-unsaturated ketone with (Z) configuration, the R-isomer of the Ir-complex leads to the formation of the isomer having R-configuration at the carbon situated in the 6-position of the hydrogenated ketone, respectively, the S-isomer of the Ir-complex leads to the formation of the isomer having S-configuration at the carbon situated in the δ-position of the hydrogenated ketone.

Finally table 7 in which (10R,E)-6,10,14-trimethylpentadec-5-en-2-one, a chiral ketone, is used, the configuration of said centre is maintained and that the chiral centers formed by the hydrogenation is in accordance with the above observations, i.e. that in the hydrogenation of an γ,δ-unsaturated ketone with (E) configuration, the R-isomer of the Ir-complex leads to the formation of the isomer having S-configuration at the carbon situated in the 6-position of the hydrogenated ketone, respectively, the S-isomer of the Ir-complex leads to the formation of the isomer having R-configuration at the carbon situated in the 6-position of the hydrogenated ketone. It also confirms that the selectivity is high when using a hydrogenation according to the present invention and the beneficial effect of 2,2,2-trifluoroethanol as compared to dichloromethane for the increase of selectivity.

TABLE 7

Hydrogenation of
(10R,E)-6,10,14-trimethylpentadec-5-en-2-one

|  | Ref. 13 | 19 | Ref. 14 | 20 |
|---|---|---|---|---|
| Formula of Ir-catalyst | Ref-A | I-D | Ref-A | I-D |
| Substrate | R-THFA | R-THFA | R-THFA | R-THFA |
| Configuration at * | R | S | R | R |
| Amount catalyst [mol-%] | 1 | 1 | 1 | 1 |
| Solvent | DCM | DCM | TFE | TFE |
| Conversion [%] | 100 | 100 | 100 | 100 |
| Isomer-Distribution[1] | | | | |
| (RR) [%] | 2.9 | 97.0 | 1.9 | 0.9 |
| (SS) + (RS)) [%] | 1.5 | 1.3 | 2.0 | 2.1 |
| (SR) [%] | 95.5 | 1.8 | 96.1 | 97.0 |

[1](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethyl pentadecan-2-one.

Examples 11, 13, 15, 17 and 19 have been used to synthesize (R,R)-isophytol and further in a high yield to a binary mixture of 2R,4'R,8'R-α-tocopherol and 2S,4'R,8'R-α-tocopherol.

Examples 10, 12, 14, 16 and 18 have been used to synthesize (S,S)-isophytol and further in a high yield to a binary mixture of 2R,4'S,8'S-α-tocopherol and 2S,4'S,8'S-α-tocopherol.

The invention claimed is:

1. A process for hydrogenation of ketones having at least a carbon-carbon double bond in the γ,δ-position to the keto group by hydrogen in the presence of at least one chiral iridium complex of formula (I)

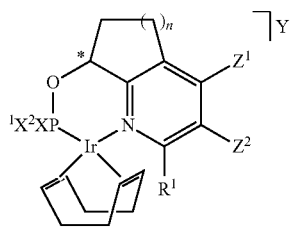
(I)

wherein n is 1 or 2;

$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;

$Z^1$ and $Z^2$ are independently from each other hydrogen atoms, $C_{1-5}$-alkyl or $C_{1-5}$-alkoxy groups;

Y is an anion selected from the group consisting of halide, $PF_6^-$, $SbF_6^-$, tetra(3,5-bis(trifluoromethyl)phenyl)borate($BAr_F^-$), $BF_4^-$, perfluorinated sulfonates, preferably $F_3C-SO_3^-$ or $F_9C_4-SO_3^-$; $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$;

$R^1$ represents a group of formula (II) or (III) or (IV):

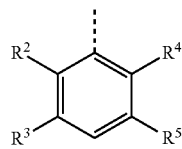
(II)

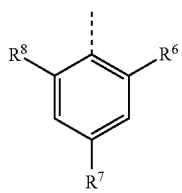
(III)

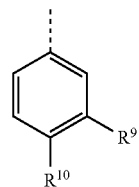
(IV)

wherein $R^2$ and $R^3$ represent either both H or an $C_1$-$C_4$-alkyl group or represent a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^4$ and $R^5$ represent a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^6$ and $R^7$ and $R^8$ represent each a $C_1$-$C_4$-alkyl group;

$R^9$ and $R^{10}$ represent a divalent group forming together a 6-membered cycloaliphatic or an aromatic ring which optionally is substituted by halogens atoms or by $C_1$-$C_4$-alkyl groups or by $C_1$-$C_4$-alkoxy groups; and wherein

* represents the chiral centre of the catalyst of formula (I); and the dotted line represents the bond by which formula (II) or (III) or (IV) is bound to the rest of formula (I).

2. The process according to claim 1, wherein $R^1$ represents formula (II a) or (II b) or (III a):

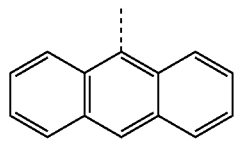
(IIa)

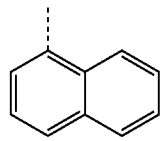
(IIb)

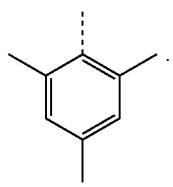
(IIIa)

3. The process according to claim 1, wherein $X^1$ and $X^2$ are both phenyl or ortho-tolyl groups.

4. The process according claim 1, wherein the catalyst is present in an amount from about 0.001 to about 5 mol % based on the amount of the ketone.

5. The process according to claim 1, wherein the chiral centre indicated by * has an R-configuration.

6. The process according to claim 1, wherein the chiral centre indicated by * has an S-configuration.

7. The process according to claim 1, wherein a ratio of molar amounts of individual enantiomers R:S of the catalyst (I) is more than 90:10 or less than 10:90.

8. The process according to claim 1, wherein the ketone is selected from the group consisting of (E)-6,10-dimethylundec-5,9-dien-2-one, (Z)-6,10-dimethylundec-5,9-dien-2-one, (5E,9E)-6,10,14-trimethylpentadeca-5,9-dien-2-one, (5Z,9Z)-6,10,14-trimethylpentadeca-5,9-dien-2-one, (E)-6,10-dimethylundec-5-en-2-one, (Z)-6,10-dimethylundec-5-en-2-one, (E)-6,10,14-trimethylpentadec-5-en-2-one and (Z)-6,10,14-trimethylpentadec-5-en-2-one.

9. The process according to claim 1, wherein the ketone has the formula (V)

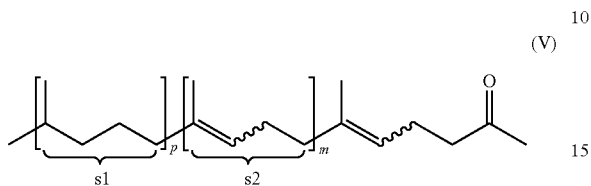

(V)

wherein m and p stand independently from each other for a value of 0 to 5, and wherein a wavy line represents a carbon-carbon bond having either a Z or a E-configuration in respect to the double bond attached to said carbon-carbon bond, and wherein substructures represented by s1 and s2 in formula (V) can be in any sequence.

10. A process of preparing isophytol comprising a step of hydrogenation of ketones according to claim 1.

11. The process according to claim 10, wherein the ketones are farnesyl acetone or geranyl acetone.

12. A process of preparing vitamin E or vitamin $K_1$ in a multi step synthesis which comprises a reaction step of hydrogenation of ketones according to claim 1.

* * * * *